(12) United States Patent
Whitcher et al.

(10) Patent No.: US 9,186,476 B2
(45) Date of Patent: Nov. 17, 2015

(54) SYSTEM AND METHOD FOR OXYGEN THERAPY

(75) Inventors: Douglas Whitcher, Woodstock, GA (US); Jeremy Blair, Atlanta, GA (US); Don Griffin, Marietta, GA (US)

(73) Assignee: RIC INVESTMENTS, LLC, Wilmington, DE (US)

( * ) Notice: Subject to any disclaimer, the term of this patent is extended or adjusted under 35 U.S.C. 154(b) by 2211 days.

(21) Appl. No.: 11/700,647

(22) Filed: Jan. 31, 2007

(65) Prior Publication Data

US 2008/0178881 A1    Jul. 31, 2008

(51) Int. Cl.
A61M 16/00    (2006.01)
A61M 16/10    (2006.01)
A61M 16/06    (2006.01)

(52) U.S. Cl.
CPC .............. *A61M 16/10* (2013.01); *A61M 16/00* (2013.01); *A61M 16/0677* (2014.02); *A61M 2202/0208* (2013.01); *A61M 2202/03* (2013.01)

(58) Field of Classification Search
CPC ....... A62B 7/06; F17C 9/02; F17C 2270/025; F17C 2270/0509; A61M 16/10; A61M 16/1075; A61M 16/1095; F25J 2215/40
USPC .................................................. 128/201.21
See application file for complete search history.

(56) References Cited

U.S. PATENT DOCUMENTS

| | | | |
|---|---|---|---|
| 4,044,133 A | 11/1977 | Myers | |
| 4,137,912 A * | 2/1979 | O'Neill | 128/204.29 |
| 5,360,000 A | 11/1994 | Carter | |
| 5,511,542 A * | 4/1996 | Hall | 128/201.21 |
| 5,839,434 A * | 11/1998 | Enterline | 128/204.23 |
| 6,085,743 A * | 7/2000 | Rosen et al. | 128/200.24 |
| 6,446,630 B1 * | 9/2002 | Todd, Jr. | 128/204.18 |
| 6,910,510 B2 | 6/2005 | Gale et al. | |
| 7,036,322 B2 | 5/2006 | Noble et al. | |
| 2002/0056451 A1 * | 5/2002 | Frankie et al. | 128/201.21 |
| 2005/0098174 A1 * | 5/2005 | Frye et al. | 128/201.21 |
| 2006/0174875 A1 | 8/2006 | Jagger et al. | |
| 2006/0219245 A1 | 10/2006 | Holder | |
| 2007/0056584 A1 * | 3/2007 | Jagger et al. | 128/201.21 |

FOREIGN PATENT DOCUMENTS

WO    WO 01/33135    5/2001
WO    WO 2006/092635    9/2006

* cited by examiner

*Primary Examiner* — Rachel Young
(74) *Attorney, Agent, or Firm* — Michael W. Haas (57) ABSTRACT

The present invention describes methods and systems to provide a liquid oxygen delivery system that efficiently delivers therapeutic oxygen in accordance with a patient's respiratory cycle. An exemplary embodiment of the present invention provides a portable liquid oxygen delivery system having a liquid oxygen device, an oxygen conserving device, and an accumulator device. The portable liquid oxygen delivery system has a collective gaseous oxygen volume and the accumulator device is enabled to actuate and reduce the collective gaseous oxygen volume.

27 Claims, 9 Drawing Sheets

SYSTEM AND METHOD FOR OXYGEN THERAPY

BACKGROUND OF THE INVENTION

1. Field of the Invention

This invention relates generally to the field of liquid oxygen storage and delivery systems, and, specifically, to systems and methods to efficiently and effectively operate liquid oxygen storage and delivery systems.

2. Description of the Related Art

A growing number of people suffer from chronic hypoxemia as a result of having a chronic obstructive pulmonary disease (COPD) such as asthma and emphysema, as well as cystic fibrosis, lung cancer, lung injuries, cardiovascular diseases, and otherwise diseased or damaged lungs. Presently, there is no cure for COPD. However, the detrimental impact of chronic hypoxemia is mitigated by the prescription of oxygen therapy in which oxygen enriched gas or pure oxygen is delivered to the airway of the user. The oxygen therapy serves to compensate for the poor function of the patient's lungs in absorbing oxygen.

The delivery of supplemental oxygen may be provided utilizing one of three predominant methods. For non-ambulatory patients, or for use during non-ambulatory periods, oxygen may be provided from a stationary oxygen concentrator, which typically makes use of a pressure swing adsorption system to generate the oxygen. Oxygen concentrators utilizing pressure swing adsorption ("PSA") systems are advantageous in that they can process ambient air, containing approximately 21% oxygen, and separate that oxygen from the ambient air. Thereby, the patient can be supplied with gas containing higher concentrations of oxygen. While suitable for their intended purpose, oxygen concentrators are generally bulky and require access to a power source, such as an electrical outlet. Thus, oxygen concentrators are ill-suited for portability and are not intended for use with an ambulatory individual.

Compressed oxygen systems are generally prescribed when oxygen is not needed all the time, such as only when walking or performing physical activity. One significant disadvantage of a compressed oxygen system is that because the oxygen is stored under pressure, the tank may be hazardous if dropped. In addition, small portable compressed oxygen tanks are limited in how long they will last depending on the prescribed flow rate and type of tank.

An alternative to compressed oxygen systems is a liquid oxygen ("LOX") system. Liquid oxygen is advantageous because it occupies a tenth of the space of compressed gaseous oxygen. To maintain a liquid state, however, oxygen must be kept at a relatively cool temperature around 300 degrees Fahrenheit below zero.

A conventional LOX system includes a large stationary LOX storage canister that stays in the home. The conventional system also includes a small, portable delivery apparatus that can be filled from the stationary unit for trips outside the home. Many first generation systems have limited utilization due to the low LOX capacity of the portable delivery apparatus and the administered LOX flow rate. Furthermore, even when not in use, the LOX within the portable delivery apparatus evaporates at a typical rate of one pound per day, thereby emptying the portable delivery apparatus LOX supply over time. Consequently, a disadvantage of a conventional portable LOX system includes the requirement that the user must return home by the end of the day to refill the portable delivery apparatus from the home stationary LOX storing canister.

Many first generation LOX systems provide a constant flow of oxygen to the patient. In these LOX systems, a flowmeter or fixed orifice can provide a desired level of oxygen to the patient at a constant flow rate. Although successful in delivering oxygen therapy at adequate levels, these LOX systems waste a significant amount of oxygen. This is due to the nature of the cycle of pulmonary gas exchange by a patient. Typically, it is only the gas inhaled during the half a second at the beginning of an inspiration that delivers oxygen to the blood stream of a patient. More specifically, it is only the oxygen that reaches the pulmonary alveoli, or spherical outcroppings of the respiratory bronchioles, that is exchanged and received within the blood stream. Therefore, for LOX systems that provide a constant flow of oxygen, the oxygen delivered at times other than the first half second of inspiration is wasted. This is highly significant to portable LOX systems that have a limited capacity of oxygen to supply to the patient.

To limit the amount of oxygen wasted by constant flow LOX system, oxygen conserving devices ("OCD") have been designed to attempt to interrupt the flow of oxygen in accordance with the patient's breathing cycle. Therefore, these oxygen conservers had to be capable of sensing inspiration by the patient to permit the therapeutic flow of oxygen during the beginning of inhalation and stop the flow of oxygen during the end of inhalation and during exhalation. It should be noted that the terms "oxygen conserving device", "conserving device", and "conserver" are used interchangeably.

Oxygen conserving devices are generally of two types, those which operate electronically, and those which operate pneumatically. Each type presents different benefits and disadvantages.

Electronic conservers require a power source, generally a battery, in order to operate, thus necessitating periodic replacement or recharging of the power source. Further, electronic conservers have integrated circuitry that most often has temperature range limitations. Electronic oxygen conservers sometimes have further disadvantages related to durability and cost.

Pneumatic oxygen conservers, however, make use of the pressurized gas and its flow within the conserver to intermittently block the delivery of gas to the person. Therefore, pneumatic conservers generally dispense with the need for power sources and complex electronics. Conventional pneumatic conservers, however, are oftentimes bulkier and generally require more complex gas lines or cannulas in order to operate.

Many conventional pneumatic conservers utilize a dual lumen cannula. Examples of conventional pneumatic conservers and their associated dual-lumen cannulas are disclosed in U.S. Pat. No. 4,044,133 to Myers and U.S. Pat. No. 5,360,000 to Carter. One lumen of the cannula is for supplying oxygen to the person wearing the cannula, whereas the other lumen generally connects to a sensing port on the conserver. The pneumatic conserver generally responds to changes in the pressure in the sensing lumen to provide oxygen to the person during inhalation and to interrupt the flow of oxygen to the person in response to exhalation. Unfortunately, dual lumen cannulas are more expensive, bulkier, and generally not as comfortable to the patient as single lumen cannulas used in electronic conservers and many other medical devices.

Conventional pneumatic conservers suffer from a significant drawback in that while they do aid in preventing the waste of some therapeutic oxygen, they often permit and even contribute to the waste of oxygen. More particularly, conventional pneumatic conserver devices typically operate by sensing negative pressure at the outlet of the conserver. When negative pressure is present at the outlet, corresponding to inhalation by the patient, the sensing valves of the pneumatic conserver will open, causing the control valves to open and permit the flow of oxygen from the output. Thus, when the patient begins inhalation, the control valve will open for the first pulse. If the patient continues to inhale, a negative pressure at the outlet will still be present and the control valves may remain open, or open again, and continue to output oxygen. As only the first half second of oxygen is therapeutic, the oxygen passed through the control valve and output after this first half second is wasted.

As a result of these and other drawbacks, pneumatic oxygen conserving devices have not enjoyed widespread use despite certain advantages of such pneumatic conservers over electronic ones. The various attempts to overcome the drawbacks of pneumatic conservers have had mixed results and have generated their own drawbacks and disadvantages.

There are a number of oxygen delivery systems that have attempted to overcome the drawbacks associated with pneumatic oxygen conserving devices. One such oxygen delivery system is disclosed in PCT application no. PCT/US00/29374 (PCT publication no. WO 01/33135)("the '374 application"). The commercial name of the product described in the '374 application is the HELiOS®. As identified at the HELiOS® website, www.heliosoxygen.com, the HELiOS® H300 portable LOX delivery unit has a limited capacity for storing a content of liquid oxygen enabling eight to ten hours of usage before the LOX is depleted when the device has a setting of two. The HELiOS® weighs approximately 3.6 pounds when full with LOX, and 2.75 pounds empty.

Another oxygen delivery system with a pneumatic oxygen conserver is the Easymate Liquid Oxygen System sold by Precision Medical, Inc. According to Precision Medical, Inc.'s website, www.precisionmedical.com, the Easymate Liquid Oxygen System is 3.6 pounds and provides a single lumen system that utilizes an oxygen conserving regulator. Furthermore, the Chad Cypress oxygen delivery system sold by Chad Therapeutics, Inc. includes a pneumatic oxygen conserver. All three of these devices, the H300, the Easymate Liquid Oxygen System, and the Chad Cypress, attempt to overcome some of the drawbacks associated with pneumatic oxygen conservers.

While suitable for their intended purposes, the prior art oxygen delivery systems with pneumatic oxygen conservers suffer from many drawbacks. The most significant drawback is that the pneumatic oxygen conservers of these oxygen delivery systems still permit oxygen to be wasted. More specifically, the pneumatic oxygen conservers generally deliver oxygen in a manner inconsistent with the oxygen consumption profiles of a person breathing through a cannula. Thus, the conventional pneumatic oxygen conservers are incapable of conserving oxygen at a desired level.

Figure 1:
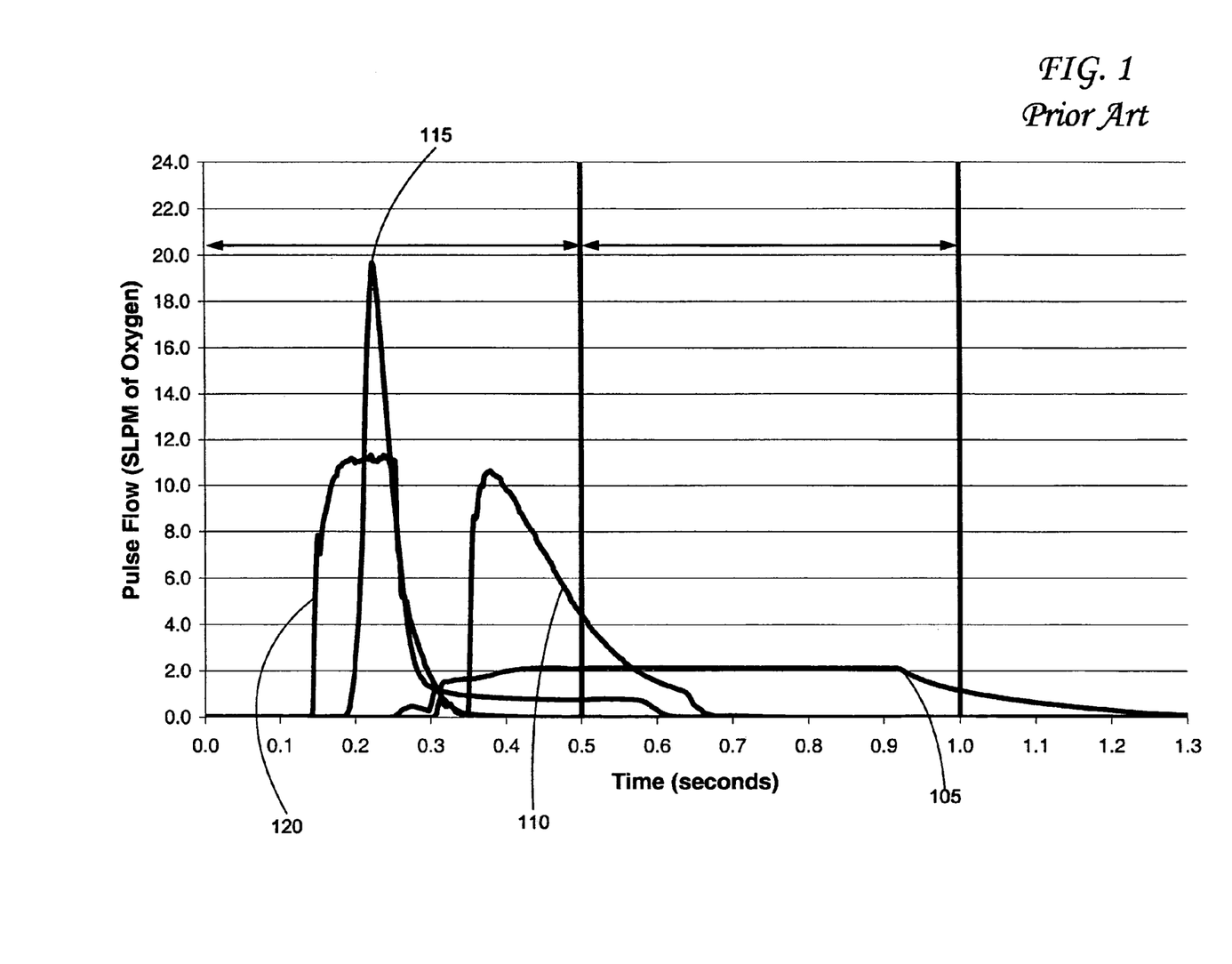
FIG. 1 is a graph illustrating the pulse flow waveforms of oxygen in standard liters per minute versus time for certain conventional oxygen delivery systems with conventional oxygen conservers.

FIG. 1 provides an illustration of the pulse flow waveform of oxygen in standard liters per minute versus time for certain conventional oxygen delivery systems with conventional oxygen conservers. In FIG. 1, the time value of zero represents the beginning of inhalation by the patient. Oxygen conserving devices are typically triggered by sensing a negative pressure, corresponding to an inhalation by the patient. Therefore, most oxygen conserving devices are configured to trigger at a negative pressure level achieved at some time period after the patient begins to inhale. The pulse flow waveforms shown in FIG. 1, provided in units of Standard Liters Per Minute ("SLPM"), are representative of delivery triggered by a typical inhalation during a patient's respiratory cycle.

Waveform 105 is a plot of the pulse flow of the Chad Cypress oxygen delivery system. As illustrated by waveform 105, the delivery of oxygen to the patient occurs at a relatively low flow rate over a relatively long period of time. As previously discussed, it is generally only the oxygen delivered within the first half second (0.5 seconds) after inspiration (time 0.0 on the graph of FIG. 1) that provides therapeutic benefit. As shown in FIG. 1, oxygen flow profile for the Chad Cypress oxygen delivery system graphed by waveform 105 does not begin until around 0.3 seconds and peaks at only 2 SLPM of oxygen. Furthermore, as shown by waveform 105, the Chad Cypress oxygen delivery system continues to provide oxygen for at least 1.2 seconds after the beginning of inspiration. The majority of the oxygen output by the Chad Cypress oxygen delivery system after 0.5 seconds is wasted. Thus, the pneumatic oxygen conserver of the Chad Cypress oxygen delivery system wastes oxygen by delivering during non-therapeutic periods of the respiratory cycle.

FIG. 1 also provides a plot of the pulse flow of Precision Medical, Inc.'s Easymate Liquid Oxygen System in waveform 110. As shown by waveform 110, the Easymate Liquid Oxygen System does not begin delivering oxygen until at least 0.3 seconds after inspiration. For delivery shown by waveform 110, the Easymate Liquid Oxygen System delivers at a rate of about 10 SPLM initially and steadily decreases from its initial peak rate. Although the Easymate Liquid Oxygen System delivers more oxygen than the Chad Cypress oxygen delivery system before 0.5 seconds after inspiration, it still continues to deliver oxygen after the 0.5 seconds mark. As shown by waveform 110, the Easymate Liquid Oxygen System continues to deliver oxygen until around 0.65 seconds. Thus, the Easymate Liquid Oxygen System wastes oxygen by delivering during non-therapeutic periods of the respiratory cycle.

FIG. 1 further provides a graph of the flow rate of oxygen by the HELiOS® H300 LOX system as waveform 115. As shown by waveform 115, the HELiOS® H300 LOX system begins delivering oxygen before the other two units at around 0.2 seconds after the beginning of inspiration. Furthermore, the HELiOS® H300 LOX system delivers a relatively large impulse of oxygen in a relatively short period in comparison to the other pneumatic devices shown in FIG. 1. More particularly, the HELiOS® H300 LOX system delivers oxygen at around 19 SLPM for an initial short impulse period and then tapers off to a lower flow rate of oxygen. For the particular delivery cycle shown by waveform 115, the HELiOS® H300 LOX system does, however, continue to deliver oxygen at around 1 SPLM for a time period after the therapeutic cutoff of 0.5 seconds.

The HELiOS® H300 LOX system, like the majority of dual lumen systems, continues to provide oxygen until the patient exhales. Therefore, the HELiOS® H300 LOX system will waste gas until the patient begins to exhale. As illustrated by the example cycle shown in waveform 115, the HELiOS® H300 LOX system continues to deliver oxygen until around 0.6 seconds. Thus, while demonstrating superior flow dynamics to that of the Easymate Liquid Oxygen System and the Chad Cypress oxygen delivery system, the HELiOS® H300 LOX system wastes oxygen by delivering during non-therapeutic periods of the respiratory cycle.

An additional waveform 120, shown on FIG. 1, illustrates a compressed oxygen system (high pressure tank system) employing an electronic oxygen conserver device, namely the Respironics' electronic Pulse Oxygen Device (ePOD™). This device is disclosed in U.S. patent application Ser. No. 11/096,993 (publication no. 2006 0219245). The ePOD system with an electronic oxygen conserver device has a distinctly different pulse image, shown by waveform 120, than those of the pneumatic oxygen conserving devices of waveforms 105, 110, and 115. The pulse flow of the ePOD electronic oxygen conserving device begins relatively quickly, around 0.15 seconds after the beginning of inspiration, and ends around 0.4 seconds. Waveform 120 illustrates that the electronic oxygen conserving device delivers a consistent burst of oxygen at around 11 SLPM for around 0.12 seconds and then quickly tapers off. Furthermore, waveform 120 illustrates that the compressed oxygen system employing an electronic oxygen conserving device does not deliver oxygen after a half second from inspiration.

The pulse of the electronic oxygen conserving device can be described as a pulse dose or box pulse, in that a relatively large amount of oxygen is delivered by a flow dynamic that starts and stops abruptly. Therefore, some electronic oxygen conserving devices can be relatively successful at delivering oxygen only during the therapeutic period of the respiratory cycle.

As shown by FIG. 1, conventional oxygen delivery systems with conventional pneumatic conserving devices, while suitable for their intended purposes, are insufficient at preventing oxygen waste. As shown by FIG. 1, the pulse dose characteristics of the oxygen delivery systems with an electronic oxygen conserving device provide an oxygen delivery pulse that is superior to that of the conventional oxygen delivery systems with pneumatic conserving devices shown in FIG. 1. As discussed above, however, oxygen delivery systems with electronic oxygen conserving devices suffer from many of their own drawbacks, relating to power consumption and complexity, among other issues.

Accordingly, a need exists for a liquid oxygen delivery system incorporating a pneumatic oxygen conserver capable of matching a patient's needs for oxygen as closely as possible. Additionally, a need exists for a pneumatic based oxygen delivery system capable of providing an oxygen delivery pulse similar to that of an efficient oxygen delivery system incorporating an electronic oxygen conserving device. In other words, a need exists for a pneumatic conserver system capable of mimicking the oxygen delivery of an electronic conserver system. Furthermore, a need exists for a oxygen delivery system capable of overcoming the drawbacks of both conventional pneumatic conserving device oxygen delivery systems and electronic oxygen conserving device oxygen delivery systems.

SUMMARY OF THE INVENTION

The present invention describes methods and systems to provide a liquid oxygen delivery system that efficiently delivers therapeutic oxygen in accordance with a patient's respiratory cycle. An exemplary embodiment of the present invention provides a portable liquid oxygen delivery system having a liquid oxygen device, an oxygen conserving device, and an accumulator device. The portable liquid oxygen delivery system has a collective gaseous oxygen volume and the accumulator device is enabled to actuate and reduce the collective gaseous oxygen volume.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF PREFERRED EMBODIMENTS

The present invention addresses the drawbacks of conventional liquid oxygen delivery systems. Significantly, the present invention provides methods and apparatus for providing a liquid oxygen delivery system that efficiently delivers therapeutic oxygen in accordance with a patient's respiratory cycle. Therefore, a liquid oxygen delivery system provided in accordance with the present invention is enabled to deliver a relatively large bolus of oxygen during an initial portion of inspiration and inhibit the delivery of oxygen during the end of inspiration and during expiration. Thereby, the present invention provides methods and systems that limit the waste of oxygen experienced with conventional liquid oxygen delivery systems.

In an exemplary embodiment, the present invention provides a portable liquid oxygen delivery system having a liquid oxygen device, an oxygen conserving device, and an accumulator device. The portable liquid oxygen delivery system has a collective gaseous oxygen volume and the accumulator device is enabled to actuate and reduce the collective gaseous oxygen volume.

In an exemplary embodiment, collective gaseous oxygen volume is the total volume of gaseous oxygen stored within the portable liquid oxygen delivery system. Therefore, in one exemplary embodiment, the sum of the volume of gaseous oxygen stored in the liquid oxygen device, a supply line to the oxygen conserving device, and the accumulator device would equal the collective gaseous oxygen volume of the portable liquid oxygen delivery system. In accordance with an exemplary embodiment of the present invention, the accumulator device is enabled to actuate and reduce this collective gaseous oxygen volume. In an exemplary embodiment, the accumulator device can be provided in communication with the supply line to the oxygen conserving device and the reduction in volume caused by the actuation of the accumulator device can maintain a predetermined minimum pressure in that supply line. In an alternative embodiment, the accumulator device can be provided in the liquid oxygen device such that a predetermined minimum pressure is maintained at the input to the oxygen conserving device.

In an exemplary embodiment, the accumulator device is enabled to maintain a predetermined minimum pressure in a supply line between the liquid oxygen device and the oxygen conserving device. Therefore, the gaseous oxygen being supplied to the oxygen conserving device is always at least above a certain predetermined minimum pressure level. In an exemplary embodiment, the oxygen conserving device of the portable liquid oxygen delivery system is enabled to sense inhalation by the patient and deliver oxygen after the beginning of inhalation. This release of oxygen by the oxygen conserving device to the patient may decrease the pressure in a supply line between liquid oxygen device and the oxygen conserving device. Some efficient pneumatic oxygen conserving devices require that a predetermined minimum pressure be maintained at the input to the device in order to maintain the proper function of the pneumatic system. Dropping below that predetermined minimum pressure can degrade or inhibit the function of the pneumatic oxygen conserving device.

To prevent these undesired effects, in an exemplary embodiment of the present invention, the accumulator device maintains a predetermined minimum pressure at the input to the oxygen conserving device when the oxygen conserving device permits the flow of oxygen to the patient after inhalation. The predetermined minimum pressure for many embodiments is the pressure below which the oxygen conserving device will no longer function properly. For example, and not limitation, the predetermined minimum pressure in one embodiment is around 5 pounds-force per square inch gauge ("psig"). In alternative example, the predetermined minimum pressure is around 10 psig. Those of skill in the art will appreciate that the predetermined minimum pressure for a system can vary according to the oxygen conserving device implemented.

In an exemplary embodiment, the accumulator device can be many different types of devices capable of dynamically changing the collective gaseous volume of the portable liquid oxygen delivery system. For example, and not limitation, the portable liquid oxygen delivery system may store a first quantity of gaseous oxygen in the liquid oxygen device, a second quantity of gaseous oxygen in the supply line to the oxygen conserving device, and a third quantity in the accumulator device. For this example, the collective gaseous oxygen volume of the portable liquid oxygen delivery system is equivalent to the sum of all three quantities of gaseous oxygen. Therefore, the accumulator device can be a device enabled to actuate and reduce the collective gaseous oxygen volume of the portable liquid oxygen delivery system. In an exemplary embodiment, the accumulator device can be enabled to reduce the volume of gas stored in the accumulator device and thus the collective gaseous oxygen volume of the portable liquid oxygen delivery system. In an exemplary embodiment, the reduction in the collective gaseous oxygen volume enables the pressure in the supply line to the oxygen conserving device to stay above a predetermined minimum pressure.

In an exemplary embodiment, the accumulator device can be a pneumatic device that does not require a power source. Therefore, the accumulator device in an exemplary embodiment can actuate based on changes in pressure within the portable liquid oxygen delivery system. In an exemplary embodiment, the accumulator device includes a piston and an accumulator chamber. The piston is enabled to actuate and reduce the volume of the accumulator chamber. The reduction in the volume of the accumulator chamber by the piston can expel a quantity of gas contained in the accumulator chamber. This quantity of gas can be inserted into the supply line connected to the input of the oxygen conserving device and thereby maintain the predetermined minimum pressure in the supply line. In an alternative embodiment, the accumulator device can be a bladder configured to reduce in size in accordance with the pressure level of the collective gaseous oxygen volume. In this embodiment, the actuation of the bladder upon a change in pressure level can reduce the collective gaseous oxygen volume of the portable liquid oxygen delivery system and maintain a predetermined minimum pressure.

After the pulse dose of oxygen is delivered to the patient by the oxygen conserving device, the system can return to a steady state. Therefore, the liquid oxygen device can pressurize the supply line back to its original steady state pressure level. In an exemplary embodiment, the pressurization of the supply line by the liquid oxygen device causes the piston of the accumulator device to return to its original open position. In this manner, the accumulator chamber is returned to its original full volume, containing enough gas to maintain a predetermined minimum pressure during the delivery of the next pulse dose. For example, and not limitation, in an exemplary embodiment the supply line can start at a pressure level of 20 psig. Once the oxygen conserving device begins to deliver a pulse dose after inhalation, the pressure in supply line of an exemplary embodiment can dip to a target pressure level. At this target pressure level, the piston can actuate and maintain pressure in the supply line above a predetermined minimum pressure of 10 psig. After the pulse dose has been delivered, the liquid oxygen device can repressurize the supply line to the steady state pressure of 20 psig. In an alternative embodiment in which the accumulator device is a bladder, the liquid oxygen device can repressurize the supply line to the steady state pressure of 20 psig and thereby return the bladder to an enlarged dimension.

Figure 2:
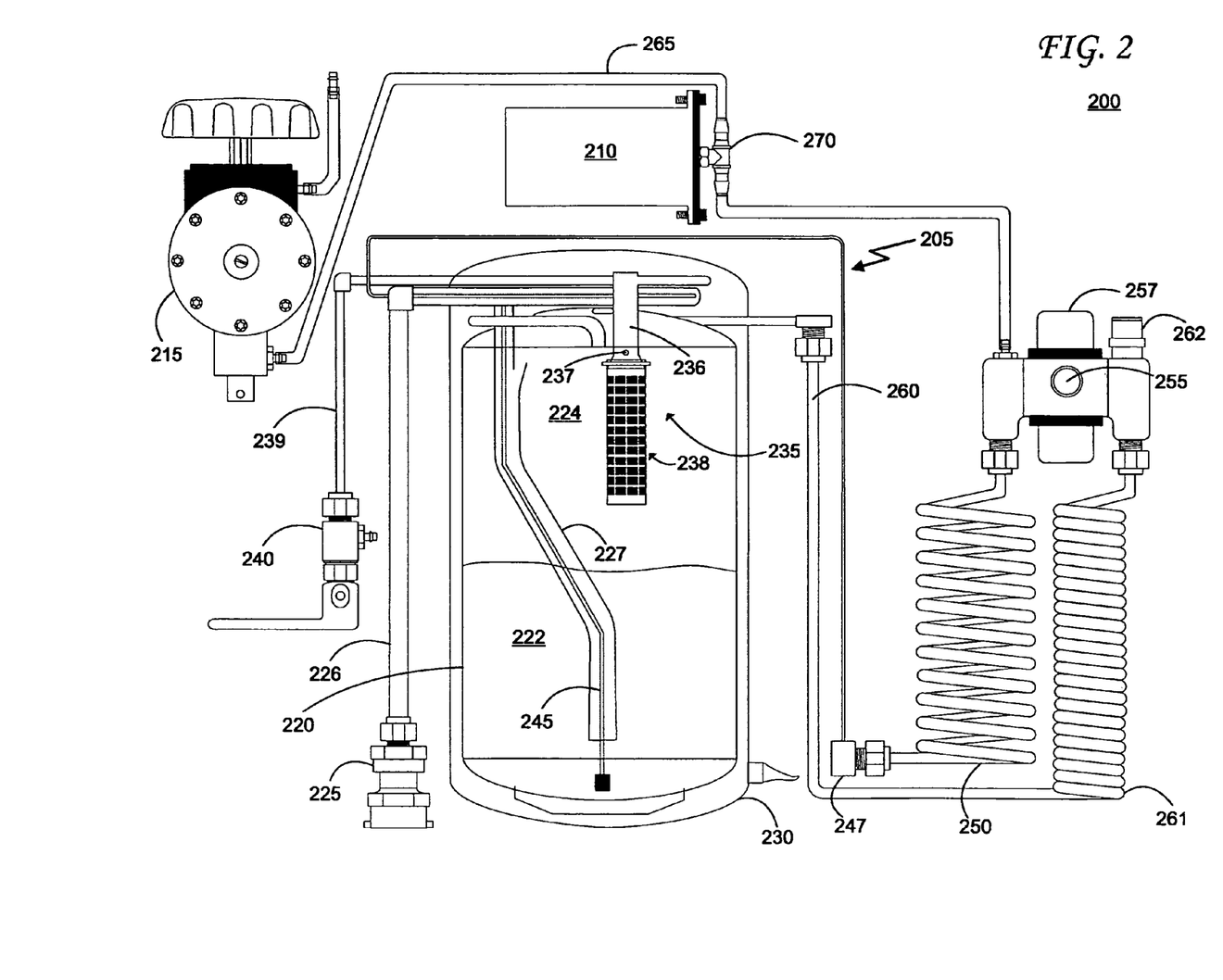
FIG. 2 is a schematic illustration of a portable liquid oxygen delivery system in accordance with an exemplary embodiment of the present invention.

FIG. 2 provides an illustration of a portable liquid oxygen delivery system 200 in accordance with an exemplary embodiment of the present invention. FIG. 2 depicts the overall system architecture of an exemplary embodiment of portable liquid oxygen delivery system 200. As shown in FIG. 2, portable liquid oxygen delivery system 200 may include three main components: a liquid oxygen device 205, an accumulator device 210, and an oxygen conserving device 215.

Liquid oxygen device 205 in an exemplary embodiment provides an area for the storage of liquid oxygen and enables for the conversion of that liquid oxygen into a gaseous state for delivery to the patient. In an exemplary embodiment, liquid oxygen device 205 includes an inner liquid oxygen container 220, which is also known as a dewar. Inner liquid oxygen container 220 may contain the quantity of liquid oxygen. A lower portion 222 of inner liquid oxygen container 220 can contain the oxygen in a liquid state, while an upper portion 224, or head space, can contain oxygen in a gaseous state.

Inner liquid oxygen container 220 of liquid oxygen device 205 can be filled by a stationary canister via a fill port 225. Fill port 225 can allow removable connection to a stationary canister of liquid oxygen. In exemplary embodiment, fill port 225 is adapted for mating engagement with discharge port of stationary LOX storage canister. Mating engagement may be via a direct connection or via a transfer conduit (not shown). Fill port 225 connects to inner liquid oxygen container 220 via a fill line 226. Fill line 226 can communicate the liquid oxygen to inner liquid oxygen container 220 via a fill tube 227. Thereby, liquid oxygen can be provided to liquid oxygen device 205 from supplemental sources. Liquid oxygen device 205 can also include an outer container 230. The space between outer container 230 and inner liquid oxygen container 220 can be evacuated to at least a partial vacuum in order to minimize heat transfer to the LOX inside inner liquid oxygen container 220.

In an exemplary embodiment, an automatic shutoff assembly 235 can be utilized during the transfer of LOX from stationary LOX storage canister into inner liquid oxygen container 220 of liquid oxygen device 205. Automatic shutoff assembly 235 can include an internal pressure release tube 236, a pressure equalizing aperture 237, a shutoff apparatus 238. Internal pressure release tube 236 can communicate with a vent tube 239 and inner liquid oxygen container 220, so that internal pressure can escape from inner liquid oxygen container 220 through the opening of internal pressure release tube 236 and into vent tube 239, wherein the internal pressure can eventually escape into the ambient atmosphere through the opened vent 240.

Shutoff apparatus 238 can be configured so that internal pressure may escape through the internal pressure release tube 236 as LOX is being filled into inner liquid oxygen container 220. As the level of LOX being flowed into inner liquid oxygen container 220 reaches a maximum capacity, shutoff apparatus 235 can be activated to prevent LOX from escaping to the ambient atmosphere. Pressure equalizing aperture 237 can communicate with internal pressure release tube 236 and inner liquid oxygen container 220. The size of pressure equalizing aperture 237 can be substantially smaller than the opening of internal pressure release tube 236. Accordingly, pressure equalizing aperture 237 can permit only a nominal amount of internal pressure of LOX to flow from inner liquid oxygen container 220 to vent tube 239.

In an exemplary embodiment, the liquid oxygen device 205 can include a liquid use tube 245. Liquid use tube 245 can be contained in fill tube 227 and can extend down into lower portion 222 of inner liquid oxygen container 220. Liquid oxygen can be permitted to pass through liquid use tube 245 to liquid use connector 247. Liquid use connector 247 can be connected to vaporizing coils 250. Vaporizing coils 250 can be configured to allow the expansion of the oxygen from a liquid state to a gaseous state for delivery to the patient. Vaporizing coils 250 can be connected to a supply line 265 and a primary relief valve 255 contained in an economizer 257.

Primary relief valve 255 can aid in preventing pressure build up within inner liquid oxygen container 220 of liquid oxygen device 205. In the event that pressure within the inner liquid oxygen container 220 of liquid oxygen device 205 exceeds a predetermined limit due to the evaporation of the LOX, primary relief valve 255 can open venting gas to the ambient atmosphere. Additionally, an exemplary embodiment of the liquid oxygen device 205 can provide a gas use line 260. The gas contained in the upper portion 224, or head space, of the inner liquid oxygen container 220 can pass through gas use line 260 to warming coils 261. Warming coils 260 can be connected to supply line 265 and a secondary relief valve 262 in economizer 257.

As shown in FIG. 2, vaporizing coils 250 and 260 can be connected to accumulator device 210 by supply line 265. Therefore, liquid oxygen device 205 can be configured to deliver gaseous oxygen to the accumulator device 210. Furthermore, accumulator device 210 can be connected to oxygen conserving device 215 via a supply line 265.

In an exemplary embodiment depicted in FIG. 2, the accumulator device 210 has an bi-directional input/output port 270. In an alternative embodiment, the accumulator device 210 has a separate input port and output port. Those of skill in the art will appreciate that the accumulator device 210 can communicate with the supply line 265 in a variety of ways without detracting from the scope of the invention.

Many different suitable types of oxygen conserving devices can be implemented as oxygen conserving device 215 depicted in FIG. 2. In an exemplary embodiment, oxygen conserving device 215 is a highly efficient pneumatic oxygen conserving device capable of delivering oxygen to a patient in a manner consistent with the oxygen consumption profiles of a person breathing through a cannula. Furthermore, in an exemplary embodiment, oxygen conserving device 215 can be a single cannula oxygen conserving device. In an exemplary embodiment, the oxygen conserving device 215 can be a device such as that fully described in PCT application no. PCT/GB2005/050043 (PCT publication no. WO/2006/092635)("the '043 application") to Concept 2 Manufacture and Design OCD Ltd., which is incorporated herein by reference.

Unlike many conventional pneumatic oxygen conserving devices, the oxygen conserving device described in the '043 application, which is also referred to as the "C2M oxygen conserving device", is enabled to efficiently and effectively deliver a bolus dose of oxygen gas to the patient before a half second after the beginning of inhalation by the patient and inhibit the delivery of oxygen in other portions of the respiratory cycle. For example, an not limitation, the oxygen conserving device taught by the '043 application is capable of delivering a pulse dose of 48 ml of oxygen to the patient before the 500 milliseconds ("ms") therapeutic cutoff. Thus, oxygen is delivered from the C2M oxygen conserving device during therapeutic periods and oxygen waste is severely limited.

Although the oxygen conserving device described in the '043 application is capable of efficiently administering a large bolus of oxygen to the patient in a short amount time, it can only do so if certain system parameters are maintained. Namely, the C2M oxygen conserving device requires that a predetermined minimum pressure of oxygen be supplied to the input of the oxygen conserving device. In some embodiments, the C2M oxygen conserving device includes an inlet regulator that provides a constant pressure to the C2M oxygen conserving device. If the pressure provided at the input to the C2M oxygen conserving device drops below that constant pressure value, then the inlet regulator of the C2M oxygen conserving device will no longer be able to provide a consistent flow and the device will function inaccurately or even fail.

The portable liquid oxygen delivery system 200 of an exemplary embodiment of the present invention can incorporate the C2M oxygen conserving device and, unlike conventional devices, maintain a predetermined minimum pressure at the input to the C2M oxygen conserving device by the use of the accumulator device 210. Those of skill in the art will appreciate that in addition to the C2M oxygen conserving device, other oxygen conserving devices capable of efficiently delivering oxygen could be substituted into portable liquid oxygen delivery system 200 of the present invention without detracting from the scope of the invention.

Figure 3:
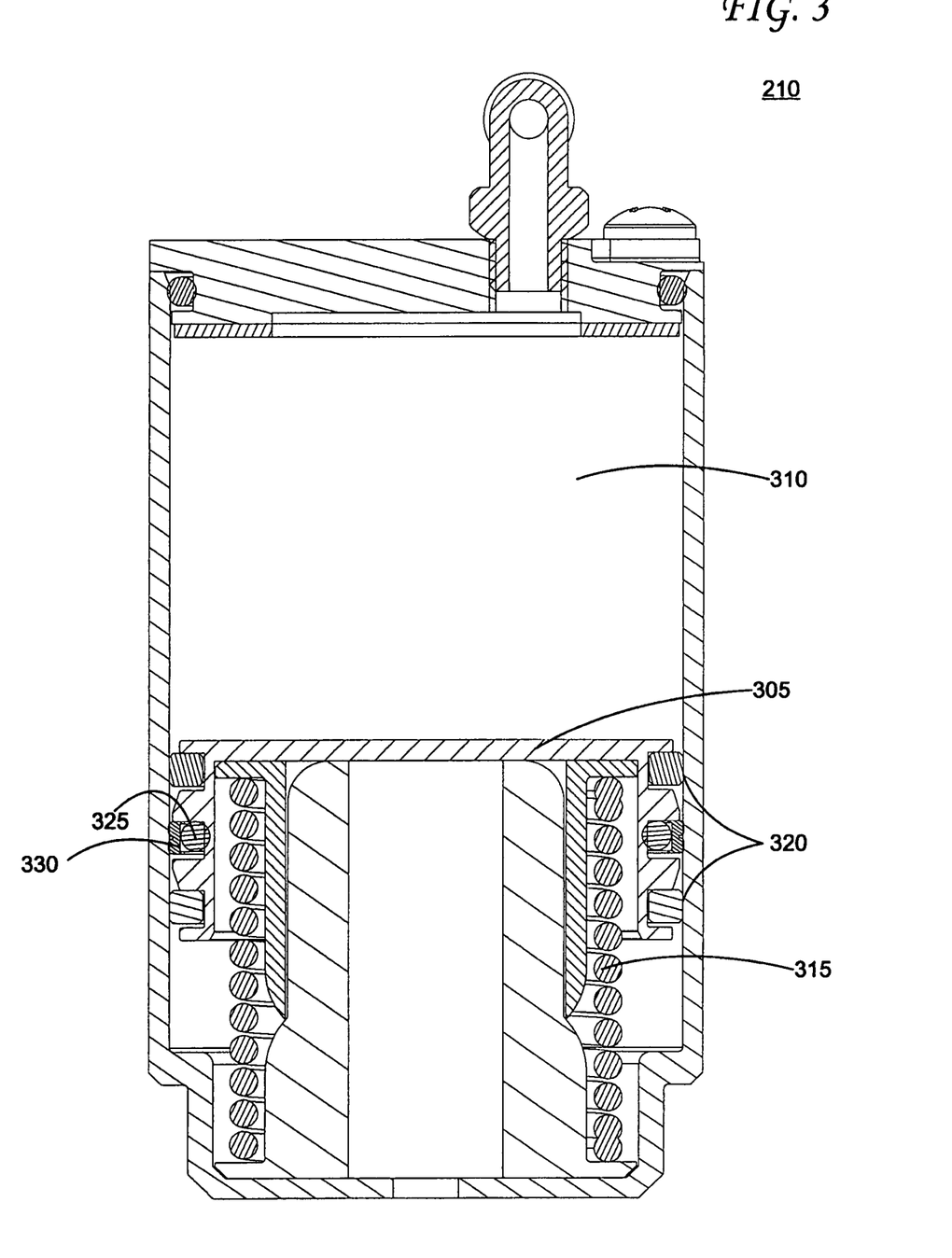
FIG. 3 is a cross-sectional view an accumulator device in accordance with an exemplary embodiment of the present invention.

FIG. 3 provides a cross-sectional illustration of accumulator device 210 in accordance with an exemplary embodiment of the present invention. As shown in FIG. 3, accumulator device 210 includes a piston 305 capable of being activated by a spring 315. In the illustrated exemplary embodiment, spring 315 encircles piston 305. Furthermore, accumulator device 210 includes an accumulator chamber 310. In the illustrated embodiment, accumulator chamber 310 is a cylindrical shaped cavity.

Accumulator chamber 310 communicates with piston 305 such that when the piston is in the fully open position, with spring 315 fully compressed, the accumulator chamber can be fully filled with gaseous oxygen. Contrastingly, when piston 305 is in the fully closed position, with spring 315 fully extended, accumulator chamber 310 contains a minimal amount of gaseous oxygen. Thereby, piston 305 can be enabled to reduce the volume of accumulator chamber 310. Those of skill in the art will appreciate that accumulator device 210 can be configured in numerous different ways without detracting from the scope of the invention.

The durability and performance tolerances of accumulator device 210 can vary according to particular implementations and embodiments of portable liquid oxygen delivery system 200. For some embodiments, portable liquid oxygen delivery system 200 may be intended for limited use implementations, and thus the durability and performance tolerances of accumulator device 210 can be relatively low. In an exemplary embodiment, however, accumulator device 210 may be relied upon to actuate for millions of cycles. Thus, the components of accumulator device 210 are required to be able to deliver consistent results without fail.

In an exemplary embodiment, piston 305 interfaces with accumulator chamber 310 via bearings 320, a seal 325, and an o-ring 330. This interface, including bearings 320, a seal 325, and an o-ring 330, enables a secure, reliable, and durable connection to the interior walls of the accumulator device 210. In an exemplary embodiment, piston 305 may be required to fire millions of times. Therefore, the internal components of accumulator device 210 must be sufficiently precise to meet these requirements. In an exemplary embodiment, the interior wall of accumulator chamber 310 in some embodiments can be machined to exact precision, providing a smooth surface containing minimal defects. Bearings 320, seal 325, and an o-ring 330 interface of the piston 305, together with the interior wall of the accumulator device 210, can ensure a tight seal with the interior wall, while at the same time being capable of repeated action. The precision and durability of the components of the accumulator device can enable the device to deliver accurate performance over millions of iterations.

In an exemplary embodiment, accumulator device 210 is connected to the supply line 265 of the portable liquid oxygen delivery system 200. Thereby, the accumulator device can be configured to maintain a predetermined minimum pressure in the supply line reducing the collective gaseous oxygen volume of portable liquid oxygen delivery system 200. In an exemplary embodiment, accumulator device 210 is enabled to actuate and reduce the volume of gas stored in oxygen conserving device 215; thus, reducing the collective gaseous oxygen volume of the portable liquid oxygen delivery system. This reduction in volume can allow for a predetermined minimum pressure to be maintained in supply line 265.

In an exemplary embodiment, oxygen conserving device 215 is enabled to sense the beginning of the inhalation by a patient. When the patient begins inhalation, oxygen conserving device 215 opens its control valve and deliver oxygen to the patient. In accordance with delivery of oxygen to the patient by the oxygen conserving device 215, liquid oxygen device 205 supplies oxygen to the oxygen conserving device via supply line 265. When oxygen is delivered by the oxygen conserving device, the pressure in the supply line can decrease. In accordance with an exemplary embodiment of the present invention, accumulator device 210 is configured to maintain a predetermined minimum pressure in supply line 265 when the oxygen is delivered by reducing the collective gaseous oxygen volume of portable liquid oxygen delivery system 200. Thus, regardless of the drop in pressure created by the delivery of oxygen by oxygen conserving device 215, a predetermined minimum pressure in supply line 265 can be maintained by accumulator device 210.

As shown in FIG. 3, accumulator device 210 is configured such that piston 305 is activated when the pressure in supply line 265 drops below a target level. Thus, the accumulator device is configured such that the steady state pressure in supply line 265 keeps spring 315 in a fully compressed position. When the patient begins inhalation and oxygen conserving device 215 begins to output oxygen, the pressure in the supply line can decrease to a target level. As a result, spring 315 becomes decompressed and permits piston 305 to travel a certain distance across accumulator chamber 310. The oxygen gas contained in accumulator chamber 310 is then released into supply line 265 and a predetermined minimum pressure is maintained in the supply line and, accordingly, the input to oxygen conserving device 215. Therefore, spring 315 can be configured with a spring constant sufficient to allow actuation of piston 305 at desired pressure levels. Those of skill in the art will appreciate, that this spring constant can vary according to the specifics of implementation without detracting from the scope of the invention. Spring 315, in an exemplary embodiment, is enabled to actuate based on changes in pressure in the system; thus, the accumulator device can be a pneumatic device that contains no powered electronics.

Accumulator chamber 310 can be many different sizes, suitable to particular implementations of portable liquid oxygen delivery system 200. For example, and not limitation, accumulator chamber 310 can be a volume equivalent to the volume of the maximum bolus of gaseous oxygen delivered by the portable liquid oxygen delivery system. In an exemplary embodiment, the maximum bolus volume delivered to the patient is 48 ml. Therefore, in this exemplary embodiment, the volume of accumulator chamber 310 is equivalent to a volume of 48 milliliters ("ml") of oxygen at atmospheric pressure (standard ml), adjusted in accordance with the increased pressure of portable liquid oxygen delivery system 200. In an alternative embodiment, liquid oxygen device 205 delivers a percentage of the bolus of oxygen and accumulator device 210 provides the remainder. In a non-limiting example, liquid oxygen device 205 can provide 10% of the maximum 48 ml bolus dose. Therefore, accumulator chamber 310 is configured to be a volume equivalent to the remaining 90% of the bolus dose. Those of skill in the art will appreciate that the dimensions and interrelationships of the components of accumulator device 210 and other components of portable liquid oxygen delivery system 200 can vary according to implementation characteristics without detracting from the scope of the invention.

Figure 4A:
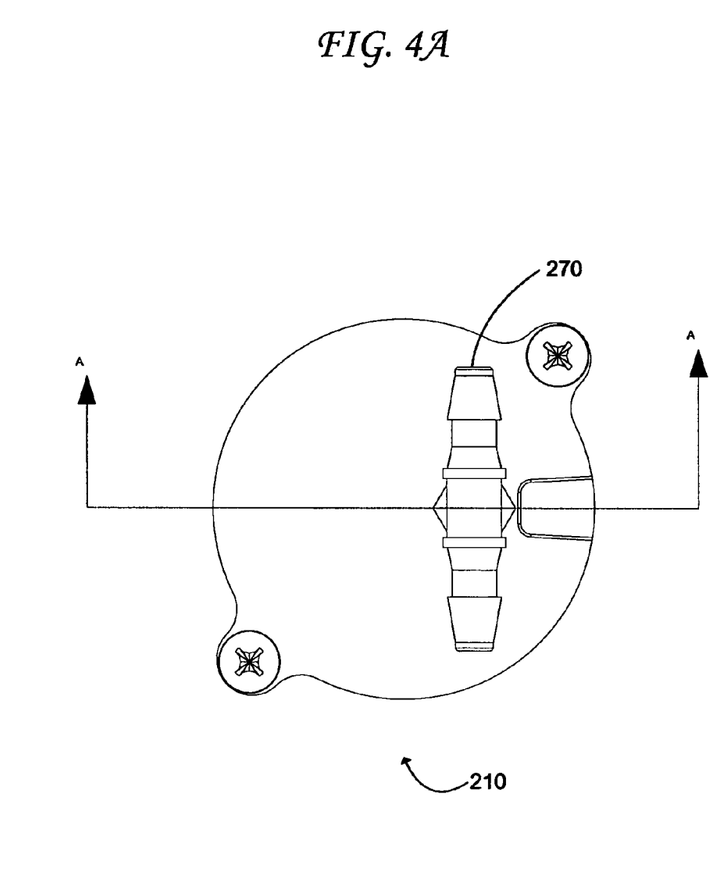
FIGS. 4A and 4B are top and side views, respectively, of the accumulator device of FIG. 3.

FIG. 4A is top view of an exemplary embodiment of accumulator device 210 in accordance with the principles of the present invention. As shown in FIG. 4A, an exemplary embodiment of the accumulator device has a single input/output port 270. In an alternative embodiment the accumulator device has a separate input port and output port. Those of skill in the art will appreciate that the type and configuration of the input and output ports for the accumulator device can device can vary without detracting from the scope of the invention. Input/output port 270 can be connected to supply line 265. Thus, oxygen gas can be communicated to and from the supply line via input/output port 270 of the accumulator device.

Figure 4B:
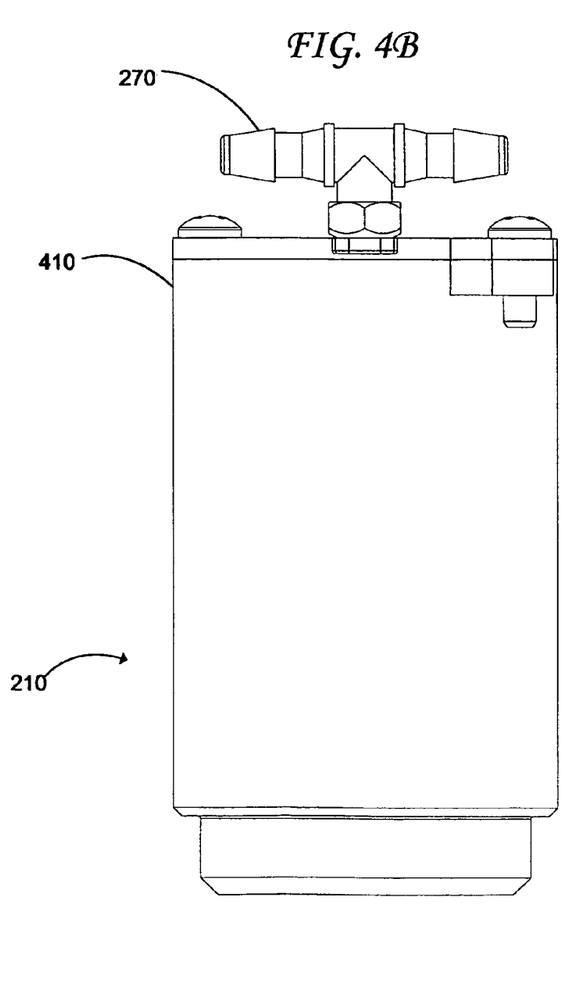

FIG. 4B is a side view of accumulator device 210 in accordance with an exemplary embodiment of the present invention. As shown in FIG. 4B, the accumulator device can include a cylindrical housing structure 410 that contains the various components of the accumulator device 210, including piston 305, accumulator chamber 310, spring 315, and other components. Cylindrical housing structure 410 can be composed of a many different materials, including metals and metal alloys capable of providing a rigid and lightweight structure enabled to withstand the severe stress that can be applied to accumulator device 210.

Figure 5:
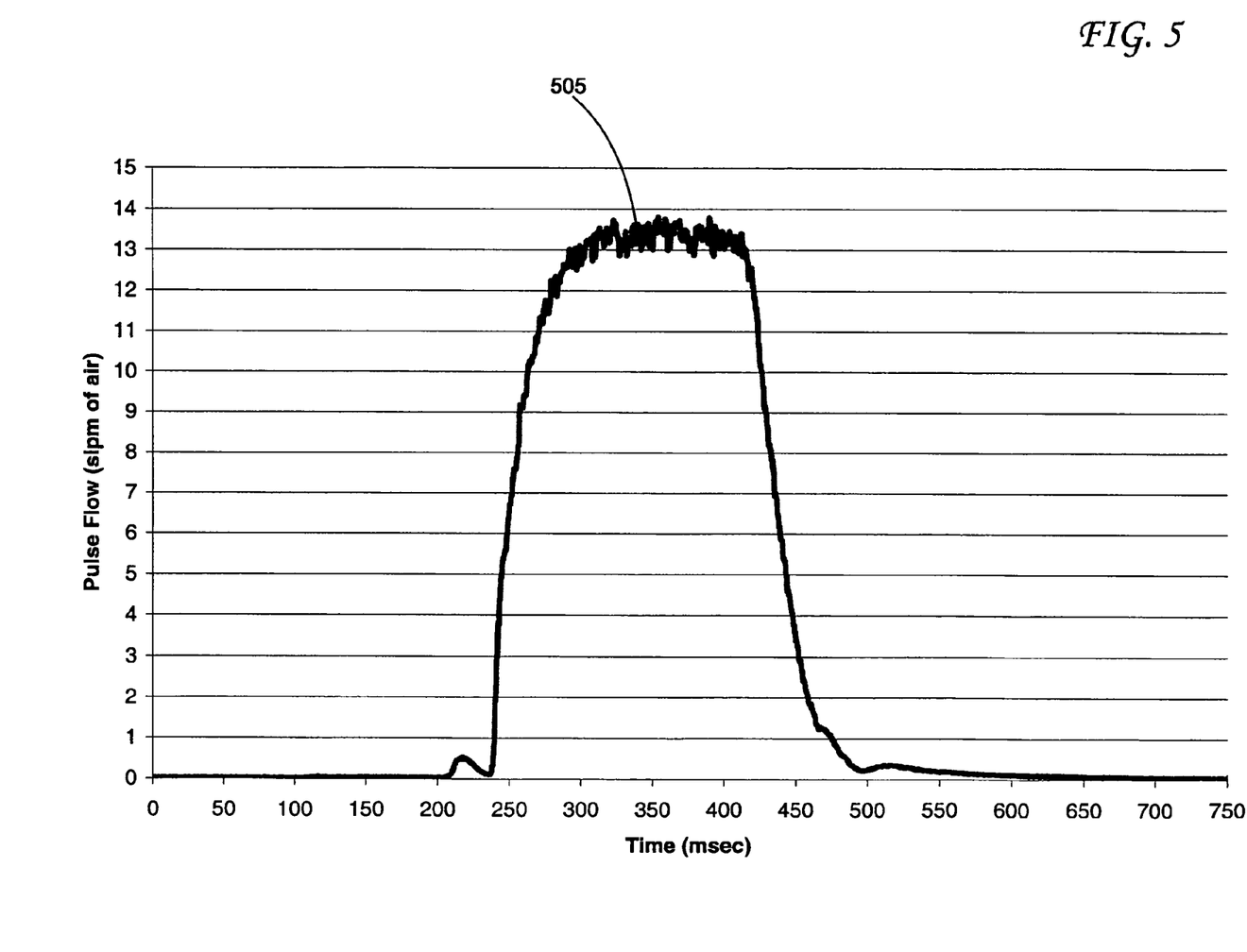
FIG. 5 is a graph illustrating the pulse flow waveform of oxygen in standard liters per minute versus time for a portable liquid oxygen delivery system in accordance with an exemplary embodiment of the present invention.

FIG. 5 is a graph illustrating the pulse flow waveform of oxygen in standard liters per minute versus time for portable liquid oxygen delivery system 200 in accordance with an exemplary embodiment of the present invention. For the exemplary embodiment of the portable liquid oxygen delivery system 200 graphed in FIG. 5, oxygen conserving device 215 of portable liquid oxygen delivery system 200 is C2M's pneumatic oxygen conserving device described in the '043 application.

As shown in FIG. 5, the flow of oxygen delivered by the portable liquid oxygen delivery system 200 mimics the efficient and effective pulse dose provided by some conventional electronic oxygen conserving devices. Thus, portable liquid oxygen delivery system 200 in accordance with an exemplary embodiment of the present invention is the first oxygen delivery system with a pneumatic conserver capable of delivering a pulse dose similar to that of a oxygen delivery system with an electronic conserver.

As shown by waveform 505, the pulse of oxygen delivery for an exemplary embodiment of portable liquid oxygen delivery system 200 graphed in FIG. 5 begins at around 200 ms after the beginning of inhalation by the patient. In FIG. 5, the time value of zero represents the beginning of inhalation by the patient. The C2M oxygen conserving device is triggered by sensing a negative pressure, corresponding to an inhalation by the patient. Therefore, the C2M oxygen conserving device can be configured to trigger at a negative pressure level achieved at some time period after the patient begins to inhale. Pulse flow waveform 505 is representative of an average inhalation pulse of the patient's respiratory cycle.

As shown by waveform 505, the pulse of oxygen delivery quickly jumps to a flow rate of around 13 standard liters per minute and remains constant at around 13 standard liters per minute for approximately 150 ms. The oxygen delivery pulse then quickly tapers off around 425 ms after the beginning of inhalation. By the 500 ms cutoff for therapeutic delivery, the flow rate delivered by the oxygen conserving device 215 of the exemplary embodiment of the portable liquid oxygen delivery system 200 is substantially zero. Therefore, the oxygen delivery pulse provided by the portable liquid oxygen delivery system, as graphed in FIG. 5, is large and rapid and occurs before the half second cutoff mark.

In an exemplary embodiment, the pulse dose, as illustrated by waveform 505, delivers a relatively large amount of therapeutic oxygen in a relatively short period of time. In an exemplary embodiment, the pulse dose shown by waveform 505 represents the delivery of a bolus of 48 ml of oxygen to the patient during the therapeutic period of the respiratory cycle, namely within 500 ms of inspiration. The pulse dose of waveform 505 shown in FIG. 5 mimics the pulse dose, or box pulse, that is only possible in the prior art with electronic oxygen conserving devices. More particularly, waveform 505 of portable liquid oxygen delivery system 200, in accordance with an exemplary embodiment of the present invention, mimics the delivery pulse of the ePOD waveform 120 shown in FIG. 1. Unlike the ePOD system, however, portable liquid oxygen delivery system 200, in accordance with an exemplary embodiment of the present invention, does not suffer from the drawbacks of an electronic oxygen conserver, which include the need for a power source (batteries), limited durability, and limited temperature operation ranges. Significantly, the portable liquid oxygen delivery system in accordance with an exemplary embodiment of the present invention is the first system capable of providing both the benefits of a pneumatic conserver oxygen delivery system and an electronic conserver oxygen delivery system.

Figure 6:
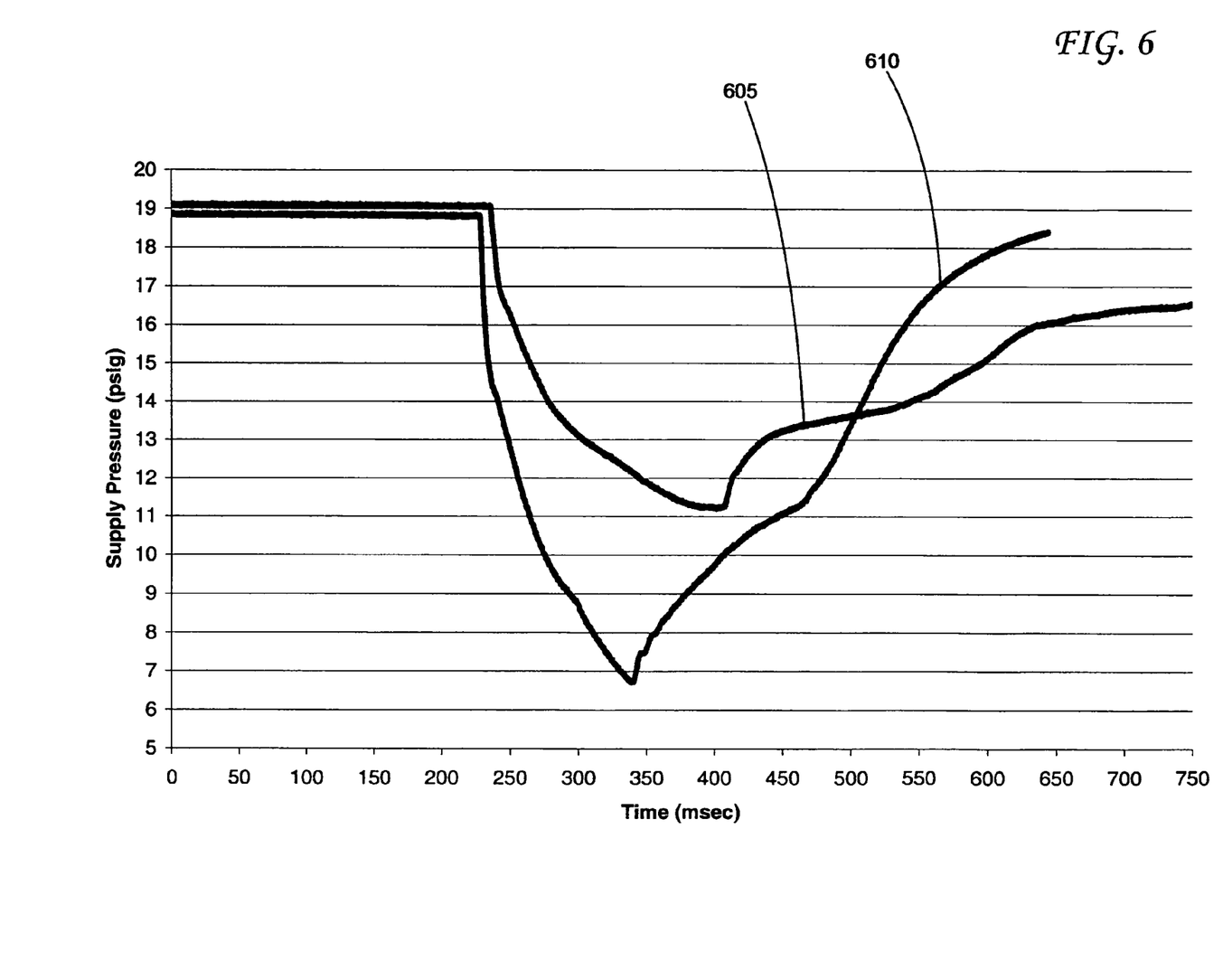
FIG. 6 is a graph illustrating two supply pressure waveforms in pounds force per square inch gauge ("psig") versus time for two portable liquid oxygen delivery systems.

FIG. 6 is a graph illustrating two supply pressure waveforms in pounds-force per square inch gauge ("psig") versus time for two portable liquid oxygen delivery systems. Waveform 605 illustrates the supply pressure for portable liquid oxygen delivery system 200 in accordance with an exemplary embodiment of the present invention. Waveform 610 illustrates the supply pressure for a LOX system without the accumulator device 210 of the present invention. For both waveforms shown in FIG. 6, the supply pressure was measured in the supply line to the oxygen conserving device.

For the exemplary embodiment of portable liquid oxygen delivery system 200, waveform 605 illustrates that the pressure in supply line, before delivery of the therapeutic dose of oxygen, is steady at about 19 psig. When oxygen conserving device 215 begins to output oxygen to the patient at about 230 ms, the pressure in supply line 265 begins to decrease. As shown by waveform 605, the pressure in supply line 265 reaches its lowest point near the end of the oxygen delivery pulse, at about 400 ms. For the exemplary embodiment shown in waveform 604, the predetermined minimum pressure reached in supply line 265 is about 11.3 psig. After reaching its minimum value, the pressure in the supply line is increased back to its original value after the pulse dose is delivered to the patient.

In accordance with an exemplary embodiment of the present invention, accumulator device 210 enables the pressure in supply line 265 to stay above a minimum valve. For example, and not limitation, this minimum value for some implementations is 10 psig. In an exemplary embodiment, it is the additional gas inserted into supply line 265 by the actuation of piston 305 and the reduction of volume in the accumulator chamber 310, that ensures the pressure in the supply line stays above a minimum level. In other words, the actuation of accumulator device 210 reduces the volume of accumulator chamber 310 and, thus, the collective gaseous oxygen volume of portable liquid oxygen delivery system 200. The reduction in the collective gaseous oxygen volume can maintain the pressure in supply line 265 above a predetermined minimum pressure. Without accumulator device 210, the pressure in supply line 265, and, thus, the input to oxygen conserving device 215, would dip below a minimum level.

Waveform 610 provides an illustration of a LOX system with a C2M oxygen conserving device but without an accumulator device 210. As shown, the LOX system without accumulator device 210 allows the pressure in the supply line to dip below the minimum level, 10 psig, for the C2M oxygen conserving device implemented. As a result, the functionality of the C2M oxygen conserving device is compromised because the device relies upon that predetermined minimum pressure value to ensure that its control and sensing valves work properly. More particularly, the input regulator of the C2M oxygen conserving device requires a constant flow of 10 psig. As shown by waveform 610, in the system without accumulator device 210, the pressure in the supply line drops below 10 psig near the beginning of the delivery of the pulse dose of oxygen at around 275 ms. Thus, for the LOX system without an accumulator device, the oxygen conserving device goes into failure almost as soon as oxygen begins to be delivered to the patient. The LOX system of waveform 610 is unable to regain the predetermined minimum pressure level required by the C2M oxygen conserving device until around 400 ms. As shown by the waveforms 605 and 610 of FIG. 6, portable liquid oxygen delivery system 200 would cease to become an efficient and effective LOX system without an embodiment of the accumulator device 210 of the present invention.

Some embodiments of portable liquid oxygen delivery system 200 can be configured for limited or even temporary use, thus relaxing the performance tolerances of the components of these embodiments. The performance tolerances of the components of other embodiments must meet exacting levels for long term use. In an exemplary embodiment, portable liquid oxygen delivery system 200 of the present invention can withstand a significant amount of stress over an extended period. As previously discussed, accumulator device 210 and its components in an exemplary embodiment, including piston 305, spring 315, bearings 320, seal 325, and o-ring 330, can maintain their integrity over millions of iterations. These consistent, precise, and reliable components can enable an exemplary embodiment of accumulator device 210 to maintain the predetermined minimum pressure in supply line 265 to the oxygen conserving device 215; thus, preventing the compromise of the performance of portable liquid oxygen delivery system 200.

To verify the sufficiency of the components of accumulator device 210, test were conducted of various exemplary embodiments of the present invention. Particularly, three embodiments of the portable liquid oxygen delivery system were monitored over the equivalent of three years of operation of the system. Table 1 below provides the results of the testing of those three units. The four operating pressures provided in the table, including (1) closed, opening, (2) open, opening, (3) open, closing, and (4) closed, closing, correspond to position of the piston 305 and the motion of piston 305 of the accumulator device 210. For example, "closed, closing," refers to piston 305 being in a fully extended and closed state after the closing motion of the piston.

TABLE 1

| Cycles (Millions) | Opening | | Closing | |
|---|---|---|---|---|
| | Closed, Opening | Open, Opening | Open, Closing | Closed, Closing |
| Accumulator #1 | | | | |
| 0.06 | 12.80 | 16.80 | 13.80 | 11.00 |
| 0.42 | 13.60 | 17.20 | 14.00 | 10.80 |
| 0.80 | 13.40 | 16.80 | 13.80 | 10.80 |
| 1.70 | 13.00 | 16.80 | 14.20 | 10.80 |
| 2.90 | 13.20 | 17.00 | 14.00 | 10.60 |
| Average | 13.20 | 16.92 | 13.96 | 10.80 |
| Accumulator #2 | | | | |
| 0.06 | 13.60 | 16.80 | 14.60 | 11.60 |
| 0.42 | 13.60 | 17.20 | 14.80 | 11.60 |
| 0.80 | 13.60 | 17.40 | 14.80 | 11.40 |
| 1.70 | 13.40 | 17.00 | 14.80 | 11.00 |
| 2.90 | 13.80 | 17.80 | 14.60 | 11.00 |
| Average | 13.60 | 17.24 | 14.72 | 11.32 |
| Accumulator #3 | | | | |
| 0.06 | 15.40 | 17.80 | 13.60 | 10.60 |
| 0.42 | 14.60 | 17.60 | 14.00 | 10.60 |
| 0.80 | 14.40 | 18.00 | 13.80 | 10.00 |
| 1.70 | 14.40 | 17.40 | 14.00 | 10.60 |
| 2.90 | 14.80 | 17.80 | 14.00 | 10.40 |
| Average | 14.72 | 17.72 | 13.88 | 10.44 |

Graphs are provided to illustrate the sufficiency of and reliability of the three exemplary embodiments of portable liquid oxygen delivery system 200 that were tested.

Figure 7:
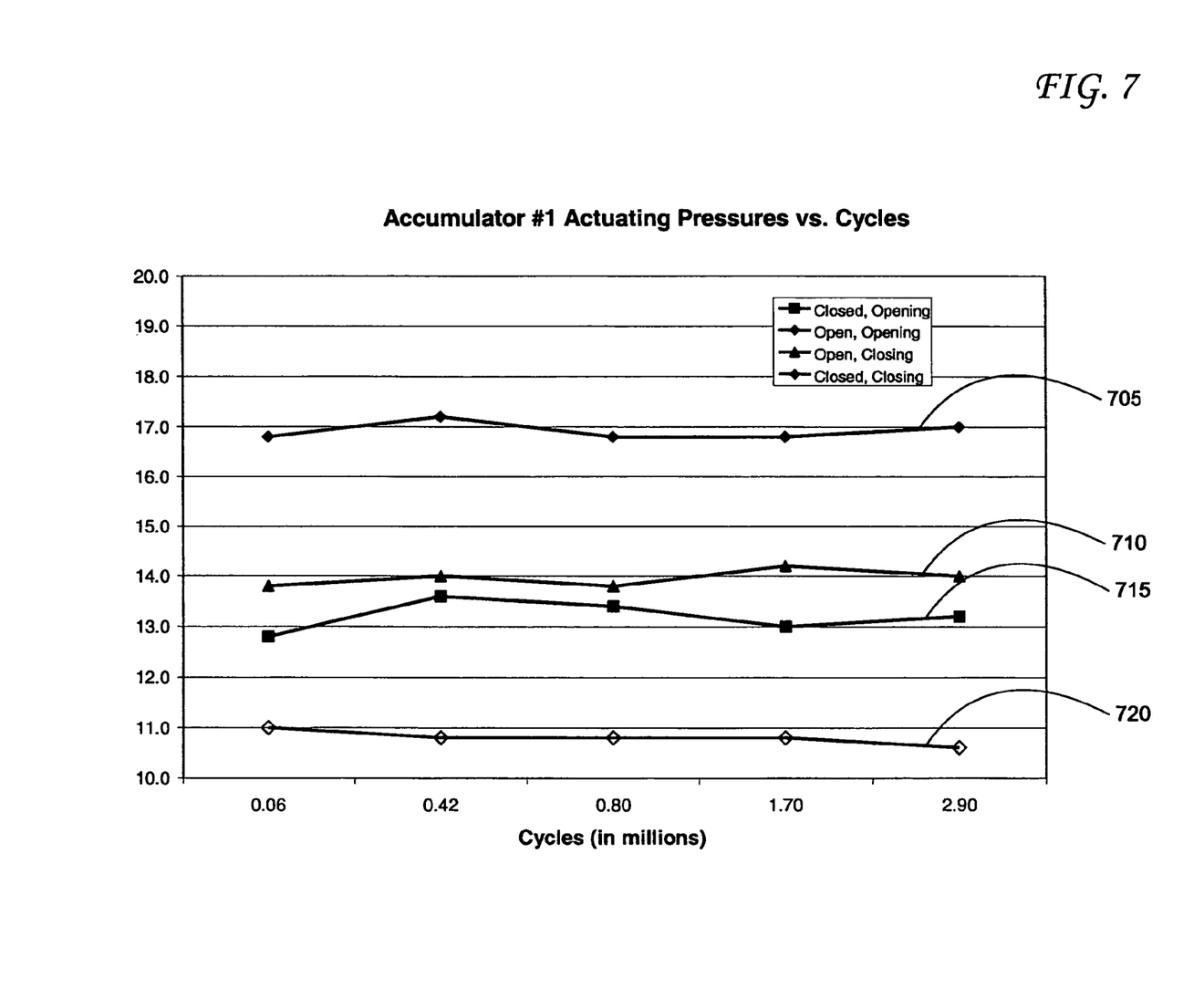
FIG. 7 is a graph illustrating four operating pressures for a first exemplary embodiment of the accumulator device 210 in accordance with the present invention.

FIG. 7 is a graph illustrating four operating pressures for a first exemplary embodiment of accumulator device 210 in accordance with the present invention. As described, the four operating pressures correspond to position of piston 305 and the motion of the piston of accumulator device 210. These four operating pressures are graphed in FIG. 7, including (1) closed, opening 715, (2) open, opening 705, (3) open, closing 710, and (4) closed, closing 720. The approximately 2.9 million cycles illustrated in FIG. 7 represent an emulation of the number of cycles performed by the accumulator device 210 over an estimated three year period. As shown by the plotlines of FIG. 7, no appreciable change is experienced in the four operating pressures of the exemplary embodiment of accumulator device 210 tested for FIG. 7 over 2.9 million cycles. Significantly, the predetermined minimum pressure level, shown by plotline 720 for the closed, closing operating pressure, never drops below the predetermined minimum pressure level for this exemplary embodiment of 10 psig over the course of 2.9 million cycles.

Figure 8:
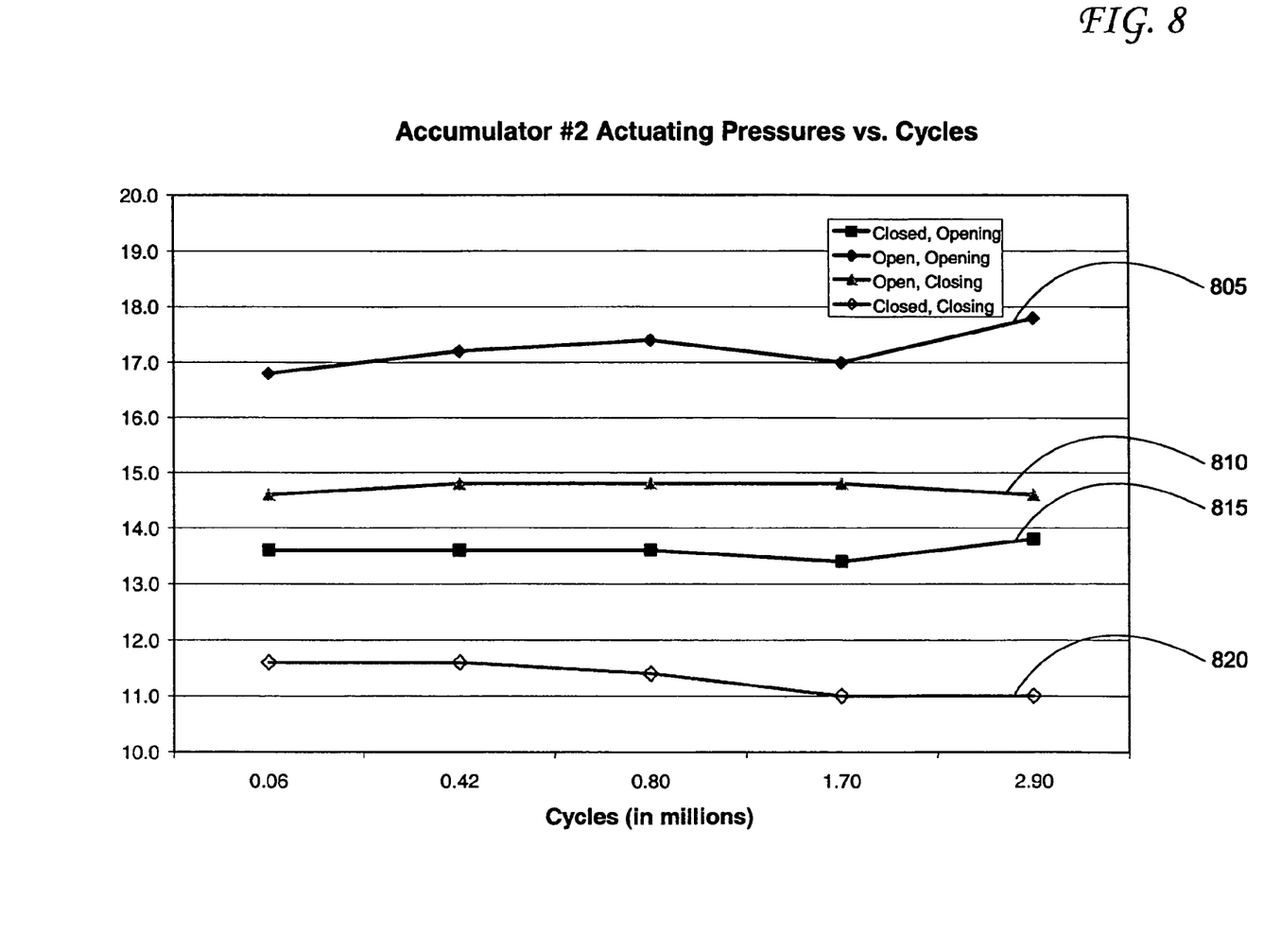
FIG. 8 is a graph illustrating four operating pressures for a second exemplary embodiment of the accumulator device 210 in accordance with the present invention.

FIG. 8 is graph illustrating four operating pressures for a second exemplary embodiment of accumulator device 210 in accordance with the present invention. Similar to FIG. 7, the four operating pressures are graphed in FIG. 8, including (1) closed, opening 815, (2) open, opening 805, (3) open, closing 810, and (4) closed, closing 820. As with the first exemplary embodiment shown in FIG. 7, the approximately 2.9 million cycles illustrated in FIG. 8 represent an emulation of the number of cycles performed by accumulator device 210 over a three year period. As shown by the plotlines of FIG. 8, no appreciable change is experienced in the four operating pressures of the second exemplary embodiment of the accumulator device 210 tested for FIG. 8 over 2.9 million cycles. Significantly, the predetermined minimum pressure level, shown by plotline 820 for the closed, closing operating pressure, never drops below the predetermined minimum pressure level for this exemplary embodiment of 10 psig over the course of 2.9 million cycles.

Figure 9:
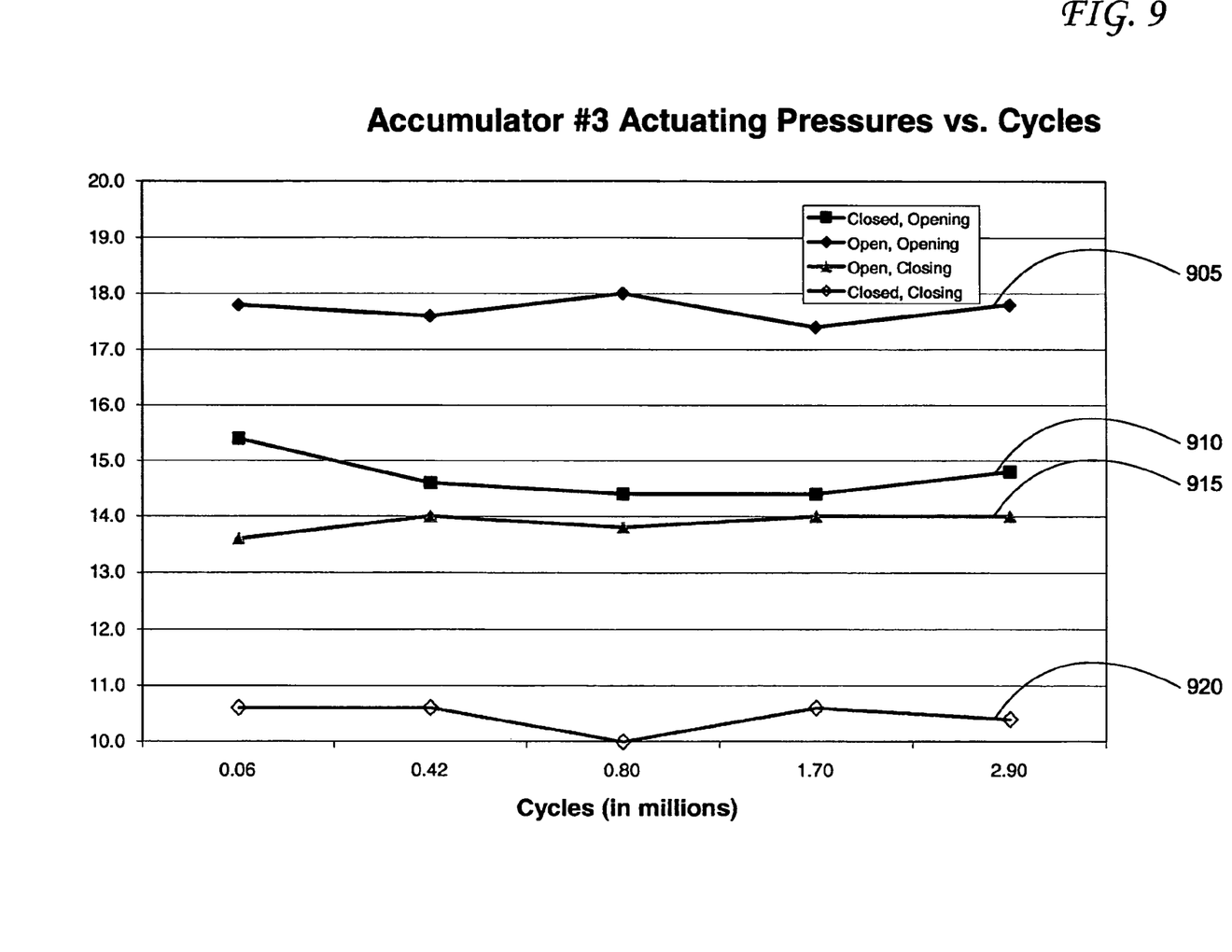
FIG. 9 is a graph illustrating four operating pressures for a third exemplary embodiment of the accumulator device 210 in accordance with the present invention.

FIG. 9 is a graph illustrating four operating pressures for a third exemplary embodiment of the accumulator device 210 in accordance with the present invention. Similar to FIGS. 7 and 8, the four operating pressures are graphed in FIG. 9, including (1) closed, opening 915, (2) open, opening 905, (3) open, closing 910, and (4) closed, closing 920. As shown by the plotlines of FIG. 9, no appreciable change is experienced in the four operating pressures of the third exemplary embodiment of the accumulator device 210 tested for FIG. 8 over 2.9 million cycles. Significantly, the predetermined minimum pressure level, shown by plotline 920 for the closed, closing operating pressure, never drops below the predetermined minimum pressure level for this exemplary embodiment of 10 psig over the course of 2.9 million cycles.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A portable liquid oxygen delivery system comprising:
    a liquid oxygen storage device;
    a pneumatic oxygen conserving device;
    a supply line communicating the liquid oxygen storage device and the pneumatic oxygen conserving device;
    an accumulator device disposed on the supply line between the liquid oxygen storage device and the pneumatic oxygen conserving device such that the accumulator device receives gaseous oxygen from the liquid oxygen storage device and provides gaseous oxygen to the pneumatic oxygen conserving device, wherein the portable liquid oxygen delivery system has a collective gaseous oxygen volume and the accumulator device is enabled to actuate and reduce the collective gaseous oxygen volume, and wherein the reduction in the collective gaseous oxygen volume by the accumulator device maintains a predetermined minimum pressure in the supply line; and
    a biasing member configured to apply a biasing force to one or more surfaces in the portable liquid oxygen delivery system, wherein the biasing force acts to decrease the collective gaseous oxygen volume.

2. The system of claim 1, wherein the predetermined minimum pressure is maintained when the oxygen conserving device delivers a quantity of oxygen to a patient.

3. The system of claim 1, wherein the predetermined minimum pressure is a pressure below which the oxygen conserving device will no longer be able to deliver a full dose of oxygen to a patient.

4. The system of claim 1, wherein the predetermined minimum pressure is at or above 5 psig.

5. The system of claim 1, wherein the predetermined minimum pressure is at or above 10 psig.

6. The system of claim 1, wherein the accumulator device includes a piston and an accumulator chamber.

7. The system of claim 6, wherein the piston is enabled to actuate and reduce the volume of the accumulator chamber.

8. The system of claim 7, wherein the reduction in the volume expels a quantity of gas contained in the accumulator chamber.

9. The system of claim 8, wherein a quantity of gas output from the accumulator device maintains the predetermined minimum pressure in the supply line.

10. The system of claim 8, wherein the supply line is enabled to be pressurized by the liquid oxygen storage device and the pressurization of the supply line causes the piston of the accumulator device to return to an open position.

11. A method of providing oxygen therapy comprising the steps of:
    providing a quantity of gaseous oxygen produced from a supply of liquid oxygen in a liquid oxygen storage device to a pneumatic oxygen conserving device through a supply line;
    delivering the quantity of gaseous oxygen to a patient during a therapeutic period of the respiratory cycle of the patient;
    changing, using an accumulator device located on the supply line between the liquid oxygen storage device and the oxygen conserving device such that the accumulator device receives gaseous oxygen from the liquid oxygen storage device and provides gaseous oxygen to the pneumatic oxygen conserving device, a collective gaseous oxygen volume between the liquid oxygen storage device and the oxygen conserving device to maintain a predetermined minimum pressure; and
    biasing a structure of the accumulator device to decrease a volume of oxygen within the accumulator device.

12. The method of claim 11, further comprising the step of pressurizing the supply line to a steady state pressure after the delivery step.

13. The method of claim 12, wherein the step of pressurizing the supply line to the steady state pressure after the delivery step is performed by the liquid oxygen storage device.

14. The method of claim 11, wherein the predetermined minimum pressure is at or above 5 psig.

15. The method of claim 11, wherein the predetermined minimum pressure is at or above 10 psig.

16. The method of claim 11, wherein the step of delivering the quantity of gaseous oxygen is performed within 500 milliseconds after the beginning of inhalation by the patient.

17. The method of claim 11, wherein the step of delivering the quantity of gaseous oxygen is only performed during the therapeutic period of the respiratory cycle of the patient.

18. An accumulator device comprising:
    a housing;
    a piston in communication with the housing;
    a biasing member configured to apply a biasing force to the piston wherein the biasing force acts to decrease a volume of oxygen within the housing; and
    an accumulator chamber within the housing, wherein the piston is enabled to reduce the volume of the accumulator chamber to expel a quantity of gas contained in the accumulator chamber, and wherein the expelled quantity of gas maintains a predetermined minimum pressure at an input port of a pneumatic oxygen conserving device, the accumulator device configured to receive gaseous oxygen from a liquid oxygen storage device and provide gaseous oxygen to the pneumatic oxygen conserving device.

19. The accumulator device of claim 18, wherein the piston is configured to expel the gas contained in the accumulator chamber when the pressure in the supply line reaches a target level.

20. The accumulator device of claim 18, wherein the piston is configured to expel the gas contained in the accumulator chamber after the oxygen conserving device begins to deliver a pulse of oxygen.

21. The accumulator device of claim 20, wherein the piston is enabled to be returned to its open position by a quantity of gas supplied by a liquid oxygen storage device.

22. The accumulator device of claim 18, wherein the accumulator chamber is in communication with a supply line from a liquid oxygen storage device to the oxygen conserving device.

23. The accumulator device of claim 18, wherein the predetermined minimum pressure is at or above 10 psig.

24. The system of claim 18, further comprising an accumulator device enabled to reduce the volume of the supply line to maintain the predetermined minimum pressure in the supply line.

25. The system of claim 24, wherein the accumulator device enabled to actuate when the pressure in the supply line reaches a target level.

26. A portable liquid oxygen delivery system comprising:
a liquid oxygen storage device containing a quantity of liquid oxygen;
a pneumatic oxygen conserving device; and
an accumulator device in communication with the liquid oxygen storage device and the oxygen conserving device such that the accumulator device receives gaseous oxygen from the liquid oxygen storage device and provides gaseous oxygen to the pneumatic oxygen conserving device, and wherein a biasing member applies a biasing force to one or more surfaces of the portable liquid oxygen delivery system, wherein the biasing force acts to decrease a volume of oxygen and enables the pneumatic oxygen conserving device to deliver a bolus of oxygen gas to a patient in less than 500 milliseconds from the beginning of inhalation by the patient, and wherein an insubstantial amount of oxygen gas is provided to the patient from the liquid oxygen delivery system after 500 milliseconds from the beginning of inhalation by the patient.

27. The system of claim 1, wherein the collective gaseous oxygen volume includes a sum of a volume of gaseous oxygen stored in the liquid oxygen device, a volume of gaseous oxygen stored in the supply line, and a volume of gaseous oxygen stored in the accumulator device.

* * * * *